United States Patent [19]

Berger et al.

[11] Patent Number: 5,406,999
[45] Date of Patent: Apr. 18, 1995

[54] RINGLESS CASTING OVAL FOR MAKING INVESTMENT MOLDS FOR PRECISION CASTING

[75] Inventors: Robert P. Berger, Encino; Steven Benson, Simi Valley, both of Calif.

[73] Assignee: Belle de St. Claire, Chatsworth, Calif.

[21] Appl. No.: 191,072

[22] Filed: Feb. 3, 1994

[51] Int. Cl.⁶ .................... A61C 13/20; B22C 7/02; B22C 9/04; B22C 21/00
[52] U.S. Cl. .................... 164/376; 164/237; 164/DIG. 4; 249/54
[58] Field of Search ............... 164/376, 237, 238, 239, 164/DIG. 4, DIG. 15; 249/54, 61, 62

[56] References Cited

U.S. PATENT DOCUMENTS

| | | | |
|---|---|---|---|
| 4,508,155 | 4/1985 | Rousseau | 164/376 X |
| 4,558,841 | 12/1985 | Engelman et al. | 164/376 X |
| 4,573,921 | 3/1986 | Berger | 164/DIG. 4 X |
| 4,777,996 | 10/1988 | Finelt | 164/376 X |
| 5,183,095 | 2/1993 | Sullivan | 164/DIG. 4 X |
| 5,360,052 | 11/1994 | Tomic et al. | 164/DIG. 4 X |

*Primary Examiner*—J. Reed Batten, Jr.
*Attorney, Agent, or Firm*—Notaro & Michalos

[57] ABSTRACT

A device for receiving dental investment solution to create an investment mold, has an oval casing which fictionally engages an oval base. Anti-rotation tabs of the base extend into anti-rotation slots in the casing, with both casing and base made of flexible plastic material.

20 Claims, 5 Drawing Sheets

RINGLESS CASTING OVAL FOR MAKING INVESTMENT MOLDS FOR PRECISION CASTING

FIELD AND BACKGROUND OF THE INVENTION

The present invention relates, in general, to casting devices for making investment molds and, more particularly, to a new and useful ringless casting oval for making investment molds for precision casting of dental prosthesis.

Investment casting, also known as precision casting, or the lost wax technique, is used in dental practice to create a casting from a wax pattern that is a duplicate of the object to be cast. The wax pattern is an acurate replica of the shape of a metal or glass dental restoration such as a gold crown, partial denture framework, metal coping for a porcelain-fused-to metal crown or a cast glass crown (e.g. the Ivoclar-Empress System). The wax pattern is attached to a second piece of wax or plastic known as a sprue.

The sprue is attached to a conical sprue former in a base to hold the wax pattern in place. A casing is then placed around the wax pattern and attached to the base to form a vessel or container into which an investment solution is poured. The investment material then hardens around the wax patterns to form the "investment mold". Removal of the base leaves a conical shape in the investment mold which will direct molten metal into the investment mold. The wax, and, if present, plastic is first removed from the mold space by placing the investment mold into an oven to melt and burn out the wax and plastic.

In many known casting mold devices, a metal or plastic casing is force fit into a groove in the base to form the vessel for holding or receiving the investment solution.

The casing may be a circular ring which fits into a circular base or the casing may be an oblong so-called oval-shaped oval which fits into an oblong or oval-shaped base to form the vessel.

In systems known as "ringless" systems, the casing is separated from the investment mold prior to the wax burnout. Ringless casting procedures eliminate many time-consuming steps associated with conventional casting procedures, which are metal casings, such as applying internal ring liners, digging burned out molds with casting out of metal rings and cleaning baked-on investment from the metal rings. The use of plastic casings from ringless molds is particularly suited to quick and easy divesting after casting and to easy cleanup. Durable plastic rings may be reused many times thereby reducing the cost per use. While techniques for oval and round casings are similar, the use of oval-shaped casings provides certain benefits in casting because investment material is used more conservatively and because the investment solution surrounds the wax pattern more uniformly which helps ensure an evenly heated investment mold and reduces the possibility of cold spots which can cause incomplete castings.

The use of flexible polymer such as polyvinyl chloride in the construction of both the base and ring is desirable, among other reasons, as such materials are more readily cleaned after the hardened investment mold is removed from the vessel.

A ringless casting oval and base device, as illustrated in U.S. Pat. No. Des. 329,900, is marketed by Belle de St. Claire of Chatsworth, Calif. The device comprises an oblong or oval-shaped casing and base, forming a vessel which receives investment solution.

In use, a wax form is mounted on the base. The casing is then inserted on or over the base. A projection provided on the inner surface of an upstanding flange engages a complementary groove formed in the outside of the casing to provide a mechanical indication that the casing is properly seated in the base.

Both the oval casing and base are composed of a flexible polyvinyl chloride. Since the polyvinyl chloride is not rigid but flexible, it may compress or distort when handled or as a result of the setting expansion, hygroscopic expansion or thermal expansion of the investment.

The Belle de St. Claire design provides a dental casting vessel which efficiently seals the investment solution within the investment vessel. However, since the casing and base are made of a flexible plastic, there may be an undesired, limited relative rotation between these parts.

Accordingly, there remains a need for improvements that includes the benefits of using a ringless casting oval without exhibiting the limited rotational tendency between the casing and base.

SUMMARY OF THE INVENTION

The present invention comprises an improved casting device for making oval-shaped investment molds for precision casting via the lost wax technique:

The device of the present invention comprises a ringless casting oval, i.e., an oval casing having a collar at an inner surface of a lower end of the casing. The base and casing of the invention are removed from the investment prior to the wax burnout step.

The casing is fictionally engageable with a base having an oval neck which extends upwardly, in an axial direction or at a slight incline for frictionally engaging the collar of the casing. A sprue former is located on the base.

The casting oval and base are composed of a flexible plastic, preferably a polyvinyl chloride, which may compress or distort when handled or as a result of setting expansion, hygroscopic expansion or thermal expansion of the investment.

Both the casing and the base are made of a plastic material. The neck of the base has an angled corner which is seated in an angled shoulder of the collar of the casing, when the casing and the base are frictionally engaged to each other.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which multiple embodiments of the invention are illustrated.

DESCRIPTION OF THE PREFERRED EMBODIMENT

The present invention pertains to a device used in the production of investment casting molds.

Figure 1:
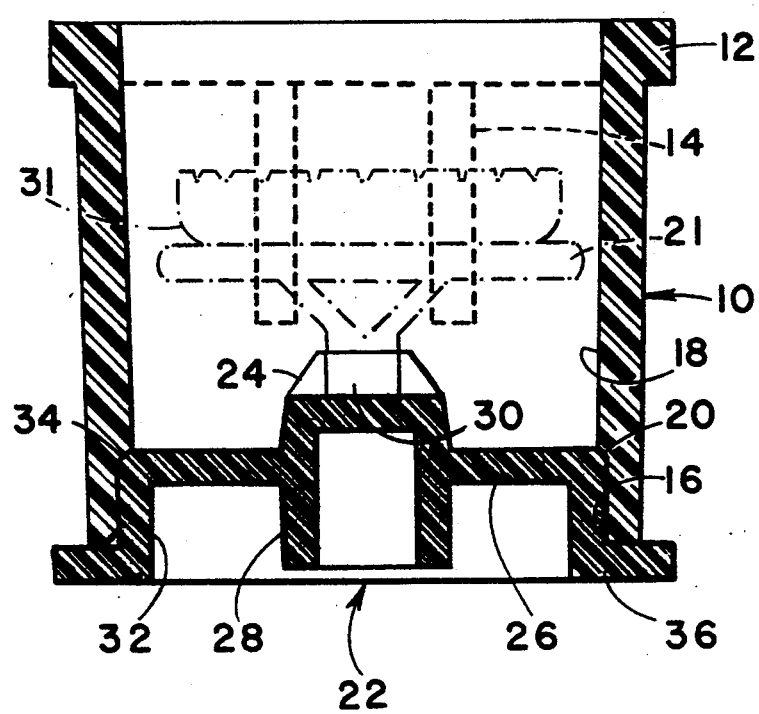
FIG. 1 is a side-sectional view of a casting device according to the present invention.
Figure 2:
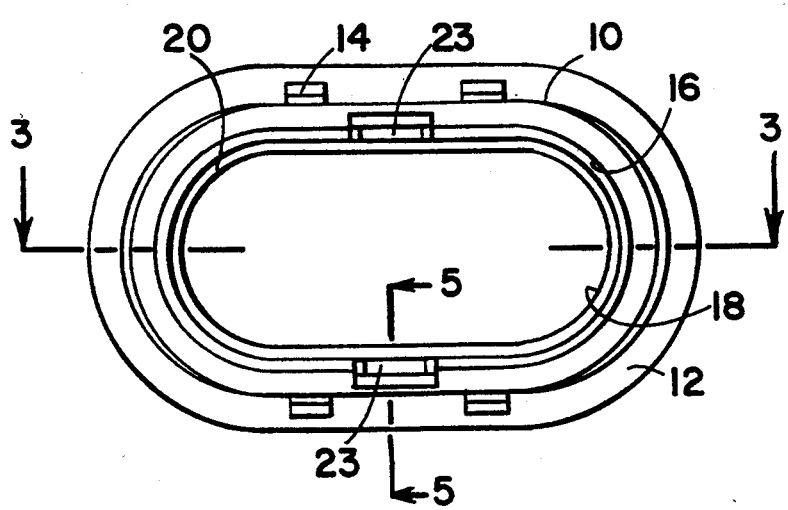
FIG. 2 is a bottom plan view of the casing of the device of FIG. 1.

As shown in FIG. 1, the present invention comprises an upper casing 10 and a lower base 22. The casing is oval in plan view and cross-section, as shown in FIG. 2. The material of the casing 10 and base 22, is plastic, in particular, polyvinyl chloride.

Figure 5:
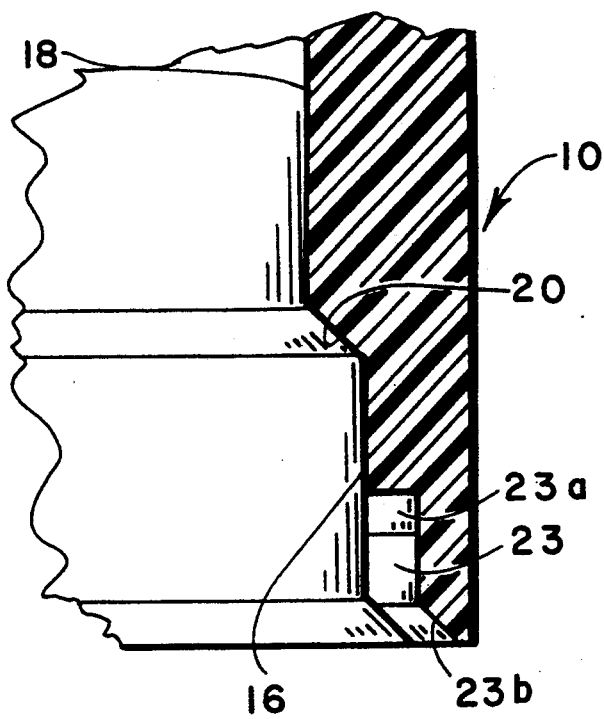
FIG. 5 is a sectional view of FIG. 2 taken along line 5—5.
Figure 6:
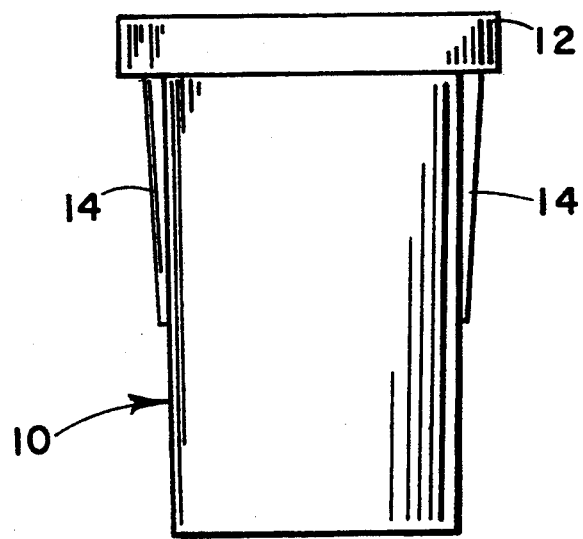
FIG. 6 is an end elevational view of the casing of FIG. 1.
Figure 7:
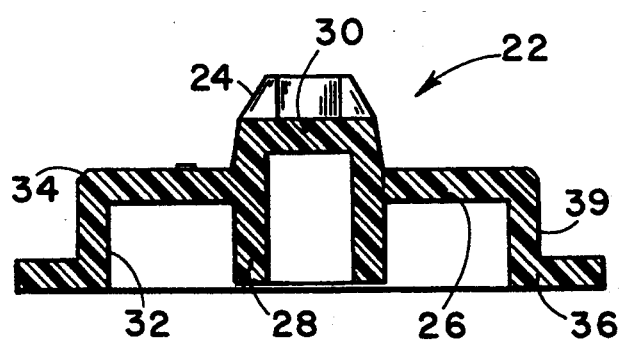
FIG. 7 is a side-sectional view of the base of the device of FIG. 1.

Casing 10 includes an upper outwardly extending radial flange 12. Two pairs of vertically extending outer supports or buttresses 14 are located on the outer surfaces of the long walls of casing 10, as shown in FIGS. 1-4 and 6. A lower inner collar 16 at the lower end of casing 10, is separated from, and slightly larger than, an inner surface 18 of the casing 10, by an angled shoulder 20 as best illustrated in FIG. 5, which is, for example, at 45° to the axis of casing 10.

Figure 8:
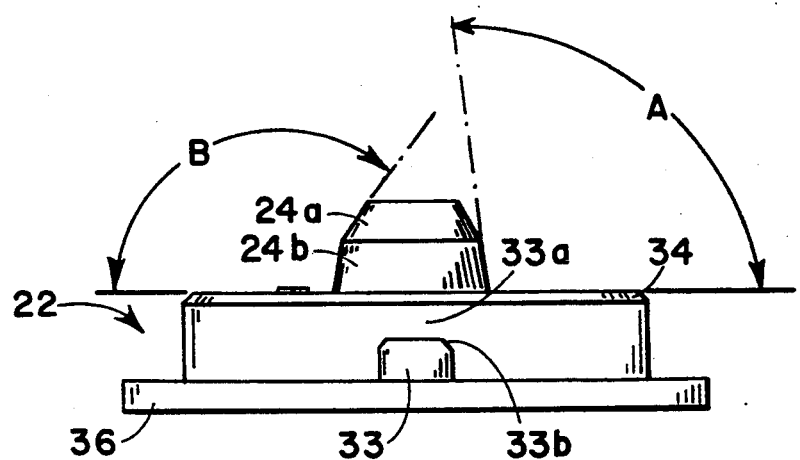
FIG. 8 is a side elevational view of the base.
Figure 9:
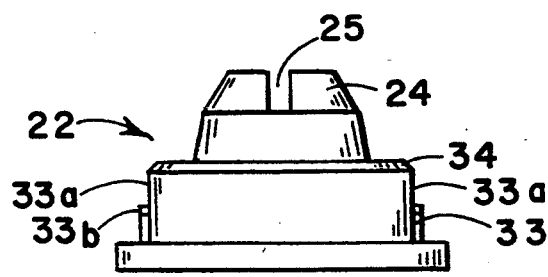
FIG. 9 is an end elevational view of the base.
Figure 10:
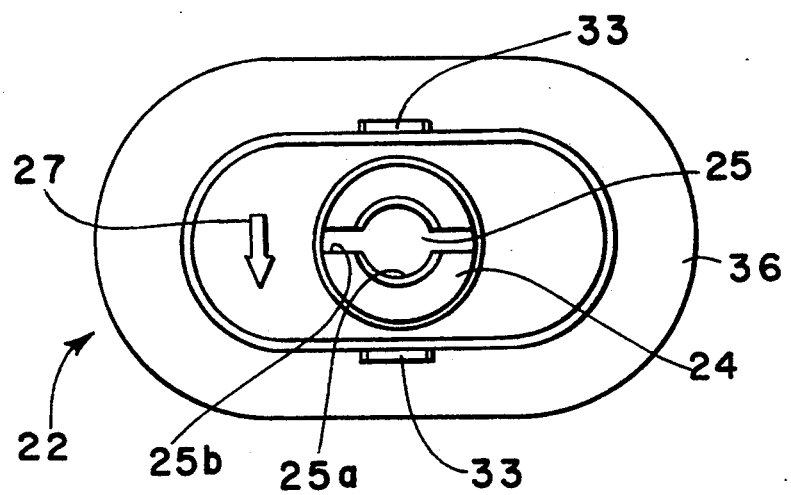
FIG. 10 is a top plan view of the base.

Base 22 includes a sprue former retainer structure 24, (as shown in FIGS. 7-10), having a sprue former slot 25 for receiving a wax or plastic sprue former shown in phantom at 21, in FIG. 1. The sprue former 21 supports a wax form, shown in phantom in FIG. 1 at 31, for use in the preparation of a lost wax casting. Slot 25 has a central cylindrical part 25a and outer diametric parts 25b as best shown in FIG. 10.

The base 22 includes a first raised floor portion 26 extending outwardly from a cylindrical hub 28. An arrow 27 is raised and on the upper surface of floor 26 to indicate the front of the wax form for casting. Hub 28 has portions extending above and below the floor 26. Retainer 24 is supported on a second raised floor portion or top 30 of the cylindrical hub 28.

A downwardly extending rim or neck 32, which is also oval, extends downwardly from the outer perimeter of floor portion 26, to a radial flange 36.

An outer surface 39 of rim 32 is in frictional engagement with the inner surface of collar 16 when base 22 and casing 10 are combined. The neck 32 extends outwardly and upwardly from flange 36 at a slight, e.g. 1°, incline or draft, which provides increased wedging and frictional engagement with collar 16 of casing 10. Collar 16 is at a 0° draft angle or may be at a slight, e.g. 1°, inward draft in a downward direction. Due to this combination of shapes, the frictional engagement of neck 32 and collar 16 has a slight tongue and groove locking effect.

Alternatively, the vertical outer wall of rim 32, rather than extending at an angle to the axis of the casing and base, extends parallel to the axis. The inner surface of collar 16 may also advantageously be parallel to the axis. A close matching of the dimensions of these inner and outer surfaces will also facilitate a firm friction fit, due to the flexibility of the plastic material making up the casing and base.

An outer angled corner 34, between floor 26 and rim 32, e.g. at 45° to the casing axis, closely receives angled shoulder 20 of casing 10. This precludes the entry of liquid investment solution into the space between the casing 10 and base 22, before the solution has cured.

Figure 11:
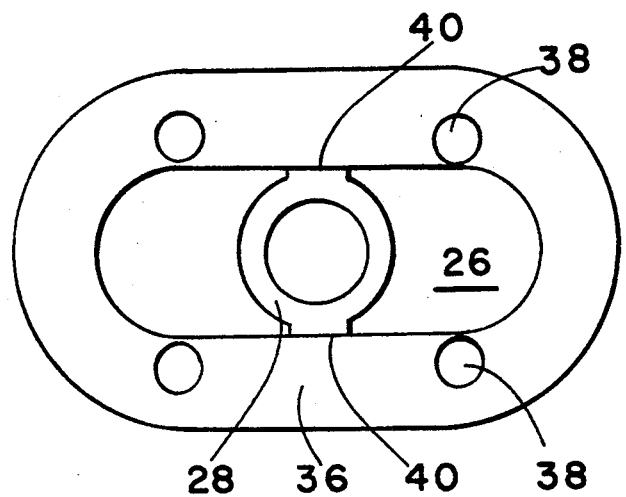
FIG. 11 is a bottom plan view of the base.

The lower outwardly extended radial flange 36 extends outwardly from the bottom edge of rim or neck 32, and has a flat bottom as best shown in FIG. 11 which serves to reinforce the base 22 and provide grasping surfaces that cooperate with flange 12 to allow a technician to firmly grasp the casing 10 and base 22, and to separate the two parts after the investment solution in the casing has cured and hardened. The bottom of cylinder 28 is slightly higher than the bottom of flange 36.

Four indented ejector pin sites 38 are spaced on the flat bottom of flange 36 to leave the inner surfaces of the base smooth to avoid undercuts in the cured investment.

Two attachment areas or ribs 40 extending between cylindrical hub 28 and the inner surfaces of rim 32, further reinforce the base.

Figure 3:
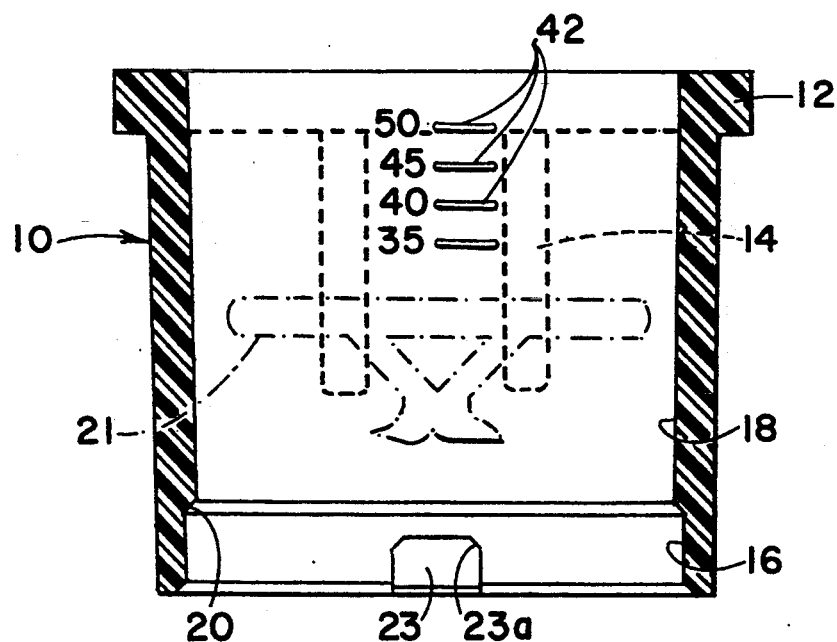
FIG. 3 is a sectional view of FIG. 2 taken along line 3—3.
Figure 4:
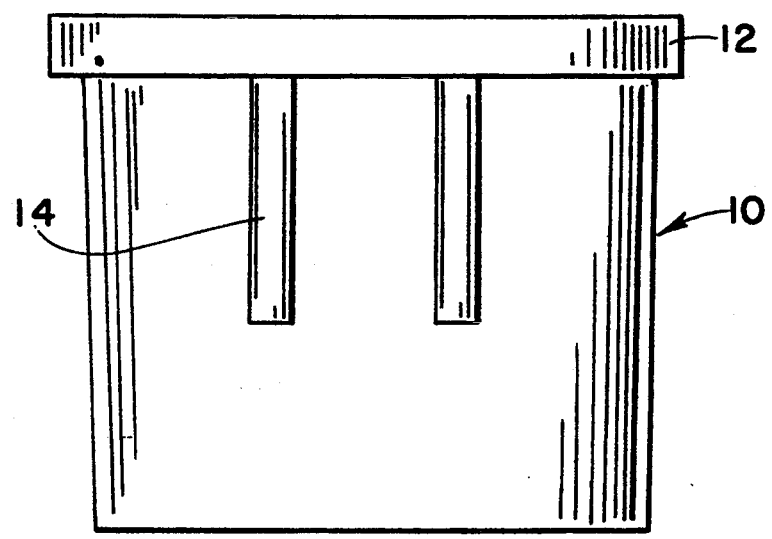
FIG. 4 is a side-elevational view of the casing.

FIGS. 2, 3 and 5 illustrate rectangular receiver slots 23 on the inner surfaces of the long walls of casing 10, which are used to receive anti-rotating tabs 33 provided on the long walls of base 22 as shown in FIGS. 8, 9 and 10.

The anti-rotation tabs 33, cooperate with slots 23, to preclude any slipping flexible rotation of casing 10 on base 22. Although both casing and base are oval, this in itself does not preclude relative rotation between these two parts because of the flexibility of the plastic material making up these parts. The invention utilizes rectangular tabs 33 on the long walls of base 22, as a positive anti-rotation lock in the rectangular slots 23 of casing 10, to prevent such relative movement.

To help avoid any leakage of liquid investment solution at the junction of tab 33 with slot 23, tabs 33 do not extend the full height of ring 32 but leave a seal area 33a above the tab. Tab 33 and slot 23 each have angled corners at 33b and 23a mate closely with each other. To help align the tab and slot, each slot 23 has an outer angled entry surface 23b best shown in FIG. 5. This helps the tab 33 which has a flat top as shown in FIGS. 8 and 9, find its way into slot 23.

To facilitate filling of the casing mold with the proper amount of investment solution, calibration markings 42 in the form of raised numerals and horizontal lines, are provided on the inner surface of the long walls of casing 10. The letters and lines are raised only slightly (for example, 0.005 to 0.010 inches) so that they can be easily read, but not so far that they obstruct removal of the cured investment from the resilient casing 10.

As best shown in FIG. 8, the upper retainer 24 extending upwardly from the floor of base 22, has a lower truncated chronicle portion 24b which extends at an angle A, for example 95° to the horizontal plane of the floor, and an upper more tapered truncated chronicle portion 24a which contains the retainer slot 25, at an angle B about 127° to the horizontal plane of the base floor.

While specific embodiments of the invention have been shown and described in detail to illustrate the application of the principles of the invention, it will be understood that the invention may be embodied otherwise without departing from such principles.

What is claimed is:

1. A device for producing an investment mold comprising:

a casing made of plastic material, having opposite open ends and an oval-cross section, the casing having an inner surface defining a casing volume and a lower inner collar separated from the inner surface by a shoulder, the collar being positioned outwardly of the inner surface with respect with an axis of the casing, the casing being thinner in wall thickness at the collar and thicker in wall thickness at the inner surface of the casing, the casing including a radially outwardly extending oval flange extending outwardly from the upper open end of the casing opposite from the collar;

a base made of plastic material, the base being oval in plan and including an oval neck with a pair of opposite long walls, the neck having an outer surface extending along the axis of the casing and in frictional engagement with the collar, the base including a cylindrical hub extending along the axis when the base and casing are fictionally engaged with each other, a first floor portion extending radially outwardly from the cylindrical hub, the first floor portion having an outer perimeter, the neck extending downwardly from the outer perimeter of the first floor portion and having a corner between the first floor portion and the neck for closely engaging the shoulder of the casing, the first floor portion of the base, the inner surface of the casing and the close engagement of the shoulder and corner forming a downwardly closed investment solution receiving volume, the base further including a radially extending flange extending outwardly from a lower end of the neck and below the casing when the casing and base are fictionally engaged with each other, and beyond the lower end of the casing, an upper portion of the hub extending above the first floor portion including a second floor portion above the first floor portion and a sprue former retainer adapted to engage and retain a sprue former; and anti-rotation means between the neck long walls and the collar for stopping relative rotation between the casing and base.

2. A device according to claim 1, wherein the shoulder is angled and corresponds in shape and size to the corner of the base which is also angled.

3. A device according to claim 2, wherein the flange of the base extends outwardly to an extend approximately equal to the extent of the flange on the casing.

4. A device according to claim 3, wherein the upper portion of the cylindrical hub is conically tapered from the first floor portion to the second floor portion by a first tapered amount, the sprue former retainer being conically tapered upwardly from the second floor portion by a second greater tapered amount.

5. A device according to claim 4, wherein the sprue former retainer comprises a slot diametrically across the retainer above the second floor portion with a central cylindrical portion and opposite diametrically extending portions.

6. A device according to claim 5, wherein the collar has opposite long walls, the anti-rotation means comprising the collar including a pair of opposite anti-rotation slots in its long walls and the neck including a pair of opposite anti-rotation tabs for engaging the anti-rotation slots to preclude relative rotation between the base and casing in the long walls of the neck.

7. A device according to claim 6, wherein each of the anti-rotation slots and tabs are substantially rectangular, the anti-rotation slots having upper square shoulders which are below the shoulder of the casing and the anti-rotation tabs having upper ends which closely mate with the shoulders of the slots.

8. A device according to claim 7, wherein the corner of each tab is angled.

9. A device according to claim 1, wherein the casing includes a pair of long walls each having outer surfaces, and at least one buttress extending vertically along each outer long wall surface to the upper outwardly extending flange of the casing.

10. A device according to claim 9, including raised calibration markings on the inner surface of the casing near an open end of the casing spaced away from the base when the base and casing are fictionally engaged with each other.

11. A device according to claim 9, wherein the shoulder is angled and corresponds in shape and size to the angled corner of the base.

12. A device according to claim 9, wherein the flange of the base extends outwardly to an extend approximately equal to the extent of the flange on the casing.

13. A device according to claim 9, wherein the upper portion of the cylindrical hub is conically tapered from the first floor portion to the second floor portion by a first tapered amount, the sprue former retainer being conically tapered upwardly from the second floor portion by a second greater tapered amount.

14. A device according to claim 9, wherein the sprue former retainer comprises a slot diametrically across the retainer above the second floor portion with a central cylindrical portion and opposite diametrically extending portions.

15. A device according to claim 9, wherein the collar has opposite long walls, the anti-rotation means comprising the collar including a pair of opposite anti-rotation slots in the long walls and the neck including a pair of opposite anti-rotation tabs for engaging the anti-rotation slots to preclude relative rotation between the base and casing.

16. A device according to claim 15, wherein each of the anti-rotation slots tabs are substantially rectangular.

17. A device according to claim 16, wherein the plastic material is polyvinyl chloride.

18. A device according to claim 1, wherein the plastic material is polyvinyl chloride.

19. A device according to claim 1, wherein the hub meets the first floor portion at an intermediate location along the length of the hub so that portions of the cylindrical hub extend both downwardly and upwardly with respect to the first floor portion, sides of the downwardly extending portion of the hub being connected to the long walls of the neck at attachment areas.

20. A device according to claim 19, wherein the anti-rotation means comprise a tab on each long wall of the neck which is less than the full height of the neck and a slot in the collar for each tab so that at least part of the collar and neck engage each other over the tab and slot.

* * * * *